United States Patent [19]
Durley, III et al.

[11] Patent Number: 5,134,359
[45] Date of Patent: Jul. 28, 1992

[54] APPARATUS FOR MEASURING ELECTROLYTES INCLUDING OPTICAL MEASUREMENTS

[75] Inventors: Benton A. Durley, III, Antioch; Carl M. Groom, Vernon Hills, both of Ill.

[73] Assignee: Abbott Laboratories, North Chicago, Ill.

[21] Appl. No.: 336,943

[22] Filed: Apr. 12, 1989

Related U.S. Application Data

[63] Continuation-in-part of Ser. No. 196,120, May 25, 1988, which is a continuation-in-part of Ser. No. 56,605, Jun. 1, 1987, abandoned.

[51] Int. Cl.$^5$ .............................................. G01N 27/50
[52] U.S. Cl. .................................. 324/71.1; 324/425; 324/96; 422/68.1; 204/416
[58] Field of Search ..................... 324/71.1, 71.5, 425, 324/438, 96, 158 D; 422/64, 72, 68, 102, 68.1; 357/25; 356/72; 350/331 R, 332, 342; 204/406, 413, 416; 455/617

[56] References Cited

U.S. PATENT DOCUMENTS

| | | | |
|---|---|---|---|
| 4,018,509 | 4/1977 | Boswell et al. | 350/342 |
| 4,316,141 | 2/1982 | Adolfsson et al. | 324/96 |
| 4,330,870 | 5/1982 | Arends | 455/617 |
| 4,502,937 | 3/1985 | Yagi | 204/406 X |
| 4,797,609 | 1/1989 | Yang | 324/158 D |

OTHER PUBLICATIONS

Schultz et al, Two-Dimensional Centrifugation for Desk-Top Clinical Chemistry, Sep. 1985, pp. 1457-1463.

Primary Examiner—Kenneth Wieder
Assistant Examiner—Jack B. Harvey
Attorney, Agent, or Firm—Karl A. Vick; Thomas D. Brainard; Richard D. Schmidt

[57] ABSTRACT

Apparatus for measuring electrolyte concentrations in fluid samples. The apparatus includes an ion selective electrode capable of generating a voltage differential having a magnitude related to the concentration of the corresponding electrolyte in the sample. A voltage to optical transducer circuit is provided to convert the voltage differentials to a digital code and then to an optical signal which is related to the concentration of the electrolytes. The optical signals are suitable for detection by conventional optical detector apparatus of assay instruments. A passive duplex transfer is utilized to simultaneously read one optical signal while transferring the next bit of the digital code. The duplex transfer configuration also makes novel use of the photodetection properties of an LED.

17 Claims, 5 Drawing Sheets

APPARATUS FOR MEASURING ELECTROLYTES INCLUDING OPTICAL MEASUREMENTS

STATEMENT OF RELATED APPLICATION

This application is a continuation-in-part of a copending, commonly owned U.S. application also entitled "Apparatus for Measuring Electrolytes", Ser. No. 196,120, filed May 25, 1988, which is a continuation-in-part of now abandoned application, U.S. Ser. No. 056,605, filed Jun. 1, 1987, the entire disclosure of both applications are incorporated herein by reference.

Other related and commonly assigned applications filed concurrently herewith include: U.S. Ser. No , 07/336,944 now U.S. Pat. No. 4,891,125 relating to a REFERENCE ELECTRODE; U.S. Ser. No. 07/337,007 now U.S. Pat. No. 4,902,399 relating to a miniature ION SELECTIVE ELECTRODE AND METHOD OF MAKING SAME; and another continuation-in-part of the above mentioned U.S. Ser. No. 196,120, relating to a TWO-PART TEST CARTRIDGE FOR A CENTRIFUGE. The entire disclosures of each of the above-identified applications are specifically incorporated herein by reference.

BACKGROUND OF THE INVENTION

1. Field Of The Invention

This invention relates generally to apparatus for measuring the concentrations of electrolyte components such as sodium, potassium, and others in fluid samples, such as biological fluids. More particularly, the invention relates to apparatus for electrically measuring the concentrations of selected electrolytes in such samples and for generating optical signals representative of the measured concentrations of the selected electrolytes. Apparatus embodying the present invention is particularly advantageous for use in conjunction with existing automated assay instruments which employ optical sources and detectors to read assays and optically encoded data, in analog and digital form.

2. Description Of Related Art

It is often necessary or desirable in determining and evaluating the condition of a patient to determine the concentration of certain electrolytes in the patient's system. Typically, the presence and concentration of electrolytes is determined by analyzing a sample of whole blood or blood serum taken from the patient. Common electrolyte components of interest include potassium, sodium, chloride, carbon dioxide, lithium, ammonium, and pH, to name a few.

Traditionally, such electrolytes have been detected and measured using flame spectrophotometric techniques. Generally, in flame spectrophotometry, a chemical composition is prepared from a sample containing the electrolyte or electrolytes of interest. The composition is then combusted and optical measurements of the resulting flame are made. The spectral characteristics of the flame ar then analyzed to determine the presence and concentration of the electrolytes of interest in the sample. The value of flame spectrophotometric techniques is limited by their ability to operate on serum only and not whole blood. In addition, in flame spectrophotometry, it is critical but very difficult to precisely control the combustion of the prepared compound. Consequently, this technique is operator intensive and it is typically not possible to obtain a high degree of repeatability.

In order to overcome the drawbacks and limitations associated with traditional flame spectrophotometric techniques, ion selective electrode apparatus and measuring techniques have been developed. An ion selective electrode typically includes a specially formulated chemical membrane connected to one of a pair of electrodes. The other electrode typically serves as a reference. The membrane is specially formulated to have an affinity for a selected electrolyte of interest. When the membrane is exposed to a fluid sample containing the selected electrolyte of interest, it attracts the electrolyte and builds up an ionic charge which results in a measurable voltage differential between the two electrodes. The electrodes may be connected to electrical circuitry which converts the voltage differential into an electrical signal representative of the concentration of the selected electrolyte. Ion selective electrodes having an affinity for most if not all of the commonly known electrolytes have been developed. Ion selective electrodes have the ability to measure electrolyte concentrations directly from whole blood samples without the requirement of first filtering the blood sample to obtain serum. In addition, ion selective electrode technology provides highly sensitive, accurate, and repeatable electrolyte measurements which are also not operator intensive.

The present invention seeks to overcome additional drawbacks and limitations inherent in the transfer of data in a centrifuge environment. More specifically, the present invention seeks to overcome drawbacks inherent in the transfer of electronic data in an environment where the source of the electronic data is in rotation with respect to a stationary recipient of the data, with speed of rotation reaching around 1800 revolutions per minute (rpm). To these ends a passive duplex data transmission configuration is provided, taking advantage of the photodetection properties of a light emitting diode. It is a significant feature of the invention that the apparatus requires little if any modification of existing automated assay instruments on which it is to be used. Advantageously, the apparatus provides the flexibility, sensitivity, accuracy, and repeatability associated with ion selective electrode technology. At the same time, the apparatus reduces costs by providing the ability to utilize the optical assay reading or optical code reading apparatus present in existing automated assay instruments without modification. Another significant feature of the invention is the relatively low cost at which the apparatus can be manufactured and used. Still other advantages and features of the invention will become apparent from the detailed description of the presently preferred embodiments thereof which is set forth below.

SUMMARY OF THE INVENTION

The foregoing features and advantages of the invention are achieved by providing an apparatus for use in an analyzer of the type having an optical source means for providing a first optical signal and first optical detector means for detecting a modulated optical signal and thereby measuring a parameter of a preselected electrolyte in a fluid sample. The apparatus comprises a cartridge having sample container means, a sensor mounted in the cartridge and in fluid tight communication with the sample container and operative when in fluid contact with the sample in order to generate an electrical signal related to a parameter of a preselected electrolyte in a sample. The apparatus further comprises a transducer circuit mounted in the cartridge and electronically connected to the sensor. The transducer is responsive to the electrical signal generated by the sensor means, and generates a second electrical signal having a parameter related to the magnitude of the first electrical signal. A second optical detector means is mounted in the cartridge and intercepts the first optical signal, generating a third signal in response to the first optical signal, with the third signal being electronically connected to the transducer to control the output of the second signal from the transducer. Optical absorbing means is mounted in the cartridge to also intercept the first optical signal. The optical absorbing means is responsive to the second signal for absorbing a portion of the first optical signal in order to generate the modulated optical signal.

The foregoing advantages are further achieved by providing the above apparatus in a centrifugal-type sample analyzer.

The foregoing advantages are still further achieved by providing, in an electronic data transfer system, a light emitting diode used as a photodetector.

BRIEF DESCRIPTION OF THE DRAWINGS

The novel features that are believed to be characteristic of the invention are set forth in the appended claims. The invention itself, together with the foregoing features and attendant advantages thereof, will be best understood by reference to the following detailed description of the presently preferred embodiments thereof, taken in conjunction with the drawings, in which:

DETAILED DESCRIPTION OF THE PRESENTLY PREFERRED EMBODIMENTS

In broad terms, the preferred embodiments of the invention comprise apparatus which is operative to electrically measure the concentrations of selected electrolytes in a biological sample and to generate optical signals representing the measured concentrations which are readable by conventional optical detector equipment. A first preferred embodiment is advantageously employed in conjunction with known automated centrifugal assay instruments of the type utilizing multichamber test cartridges and conventional optical source and detector apparatus such as photomultiplier tubes (PMT).

A second and equally preferred embodiment is advantageously employed in conjunction with known automated centrifugal assay instruments of the type utilizing multichamber test cartridges and conventional optical source and detector apparatus such as PMT's. In addition, the second embodiment utilizes a duplex transfer configuration for transfer of data between the test cartridge and a VISION instrument (Abbott Laboratories, Abbott Park, Ill.) and makes novel use of the photodetection properties of an LED. An exemplary application of the first and second preferred embodiments to a typical instrument of this type is also described in detail below.

It is understood, however, that the broad principles of the invention are not limited by the particularly advantageous applications of the preferred embodiments. Rather, the broad principles of the invention are applicable to other types of existing automated instruments, to stand-alone, non-automated applications with optical reading apparatus, and to many other applications where it is necessary or desirable to measure assays electrically and to read the measurements optically. It is also understood that application of this invention is not limited to use with biological fluids but is also applicable to any sample in which it is desirable to measure some parameter, condition or characteristic of the sample.

FIGS. 1-4 illustrate a first embodiment of the electrolyte measuring apparatus of the invention. The first embodiment generally comprises ion selective electrode means 200 for generating a plurality of voltage differentials corresponding to the concentrations of a corresponding plurality of pre-selected electrolyte concentrations in a sample, transducer circuit means 210 for converting the voltage differentials to electrical signals having parameters related to the magnitudes of the voltage differentials, and optical output means 220 responsive to the electrical signals to generate optical signals having parameters related to the parameters of the electrical signals and representative of the concentrations of the pre-selected electrolytes in the sample. The ion selective electrode 200 is preferably constructed according to the teachings of co-pending applications U.S. Ser. No. 196,120 and U.S. Ser. No. 07/337,007 now U.S. Pat. No. 4,902,399, previously identified and incorporated herein by reference. In the first preferred embodiment, the magnitudes of the electrical signals and the optical densities of the output optical signals relate to and are representative of the concentrations of the selected electrolytes in the sample. The optical output means 220 is operative in response to the electrical signals to selectively absorb light from an optical source 225 in order to generate optical signals readable by an optical detector 230 such as a PMT.

Figure 1:
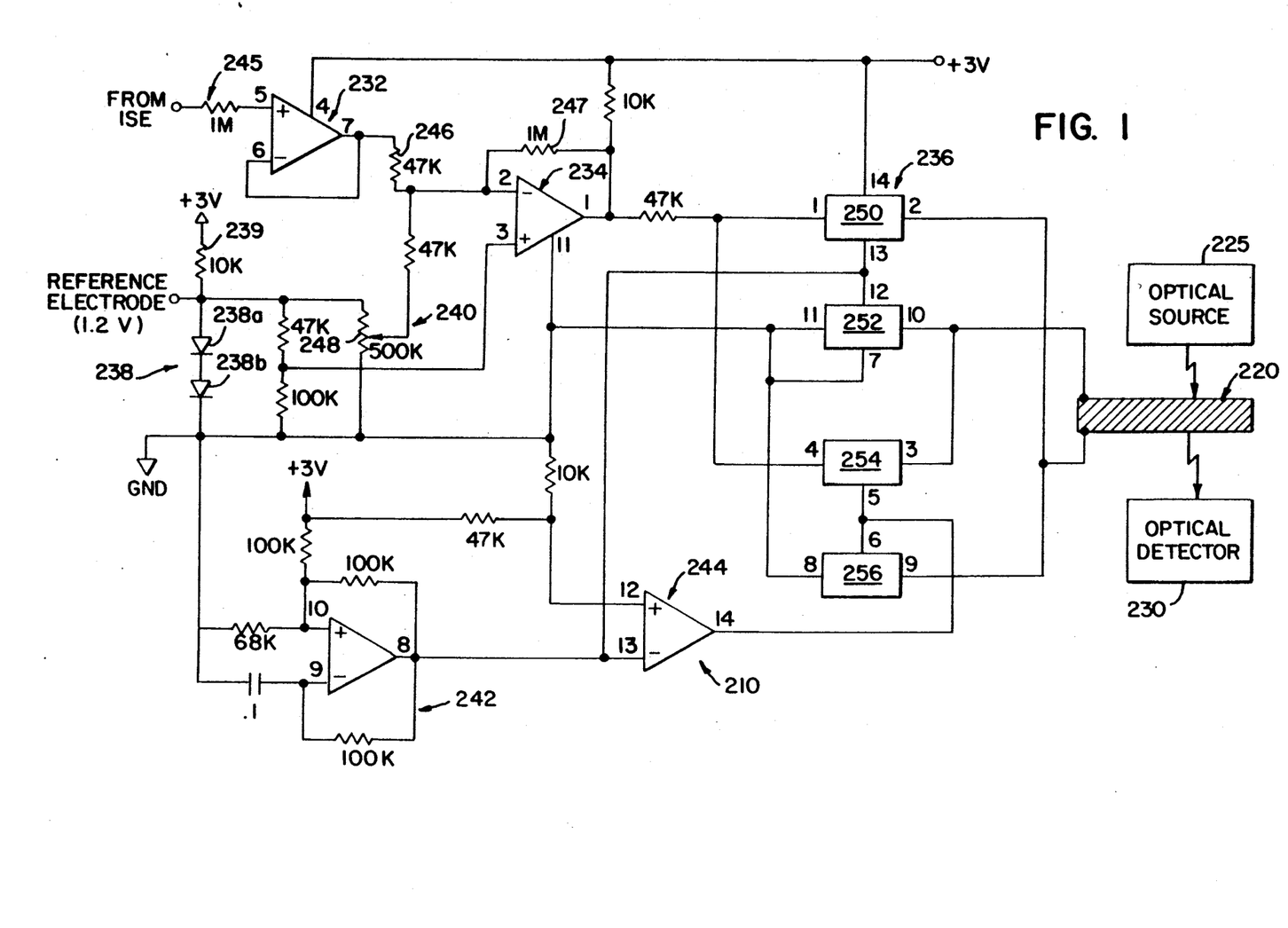
FIG. 1 is an electrical schematic diagram illustrating the details of an optical output means and a transducer circuit for converting voltage potentials on the ion selective electrodes to optical output signals comprising a portion of a first preferred embodiment of the electrolyte measuring apparatus of the invention.

Referring to FIG. 1, an electrical schematic diagram illustrating the details of the transducer circuit means 210 and optical output means 220 is shown. For convenience, the transducer circuit means 210 is illustrated as receiving only one input from the ion selective electrode 200. It is understood, however, that the transducer circuit means 210 is operative to sequentially process a plurality of voltage differentials generated by the ion selective electrode 200 by multiplexing the voltages in the same manner as described in previously referenced co-pending U.S. Ser. No. 196,120. The transducer circuit means 210 generally comprises high impedance input buffer means 232, linear amplifier means 234, bilateral switch means 236, voltage reference means 238, offset adjustment means 240, oscillator means 242, and inverting driver means 244. The input buffer means 232 is suitably comprised of an operational amplifier configured as a source follower as illustrated having its non-inverting terminal connected to the ion selective electrode 200 to receive a voltage differential generated thereby through a 1 Mohm resistor 245. The input buffer means 232 provides high impedance isolation between the ion selective electrode 200 and the transducer circuit means 210 to prevent the flow of current through the detection sites of the ion selective electrode 200.

The output of the input buffer means 232 is connected to an input of the linear amplifier means 234. The linear amplifier means 234 is preferably comprised of an operational amplifier having its inverting terminal connected to the output of input buffer means 232 by a resistor 246. The gain of the linear amplifier 234 is determined by the values of the resistor 246 and a feedback resistor 247, the values of which are preferably selected to maintain the response of the transducer circuit means 210 within the linear operating range of the optical output means 220, which is described in detail below. The values illustrated for resistors 246 and 247 have been found to provide adequate linearity with the preferred ion selective electrode 200 and optical output means 220 which are described in detail below.

Also connected to the inverting terminal of the operational amplifier 234 is the output of the offset adjustment means 240, which includes a variable resistor 248. Similarly to the offset adjustment means described in previously referenced U.S. Ser. No. 196,120, the offset adjustment means 240 provides a variable voltage at the inverting terminal of the linear amplifier 234 to adjust the response of the amplifier 234 for a range of ion selective electrode output signal levels. The variable resistor 248 of the offset adjustment means 240 is preferably adjusted to maintain the response of the linear amplifier 234 within the linear operating range of the optical output means 220. As described in previously referenced U.S. Ser. No. 196,120, the variable resistor 248 of the offset adjustment means 240 may be replaced by fixed resistor values if an ion selective electrode 200 having known output signal levels is employed.

The output of the linear amplifier 234 is connected in parallel to two inputs of the bilateral switch means 236. The bilateral switch means 236 preferably comprises four parallel solid state switches 250, 252, 254, and 256. The switches are preferably packaged in a single integrated circuit part No. HEF4066 or equivalent. The switches are preferably controlled in pairs with switches 250 and 252 comprising one pair and switches 254 and 256 comprising a second pair. The inputs of one switch from each pair, i.e., switches 250 and 254, are connected in parallel to the output of the linear amplifier means 234. The inputs of the remaining switch from each pair, i.e., switches 252 and 256, are connected to ground. The outputs of the switches 250 and 256 are connected in parallel to one terminal of the optical output means 220 and the outputs of the switches 252 and 254 are connected in parallel to a second terminal of the optical output means 220. The control terminals of the first pair of switches 250 and 252 are connected to the signal input of the inverting driver 244 and the control terminals of the second pair of switches 254 and 256 are connected to the output of the inverting driver 244 so that only one pair of switches is actuated at any time.

The optical output means 220 is preferably a liquid crystal light valve of the type known to those skilled in the art. A suitable light valve having desirable high impedance, low voltage, and large linear dynamic range characteristics is available from UCE, Inc. of Norwalk, Conn. The selected light valve preferably has a transparent to opaque range in excess of three optical density units. The liquid crystal light valve is preferably driven by an AC source, preferably a square wave, to prevent the tendency of the light valve to drift back to its quiescent transparent condition after a short time when a DC drive signal is utilized.

The oscillator means 242 preferably comprises an operational amplifier feedback oscillator configured as illustrated to provide a 60 Hz. square wave signal. The output of the oscillator 242 is connected to the signal input of the inverting driver 244, which is preferably an operational amplifier configured as illustrated, and to the control terminals of the first pair of bilateral switches 250 and 252. The operational amplifiers of the oscillator 242, driver 244, input buffer means 232, and linear amplifier 234 are preferably provided in a single integrated circuit package, part no. TLC25L4 or an equivalent. The oscillator 242 and inverting driver 244 alternately actuate the first and second pairs of bilateral switches at a rate of 60 Hz. to drive the liquid crystal light valve 220 with alternating polarities of the electrical signal appearing at the output of the linear amplifier 234. The response time of the preferred liquid crystal light valve is such that it cannot respond to the alternating polarity of the drive signal at the 60 Hz. rate, but rather maintains a substantially fixed degree of opaqueness which is linearly related to the absolute magnitude of the alternating polarity drive signal.

The transducer circuit means 210 of the first embodiment is suitably supplied by a single cell lithium battery having an output voltage of approximately +3 volts. The transducer circuit means 210 of the first embodiment generates a reference voltage of approximately 1.2 volts from the supply voltage and applies the reference voltage to the reference electrode of the ion selective electrode 200. The voltage reference means 238 comprises a pair of series diodes 238a and 238b which are connected in series between the supply voltage and ground in series with a 10 K ohm current limiting resistor 239. The reference voltage is taken between the cathode of the first diode 238a and ground.

The first embodiment is particularly advantageously employed in conjunction with existing automated centrifugal assay instruments of the type employing a multichamber test cartridge and conventional optical source and detector apparatus. An exemplary instrument of this type is the VISION ® automated centrifugal assay instrument manufactured and sold by Abbott Laboratories of Abbott Park, Ill. The interfacing and utilization of the first embodiment with the VISION ® instrument will now be described, it being understood that the VISION ® instrument is merely illustrative and that the first embodiment is also advantageously employed in conjunction with other automated assay instruments having the general characteristics identified as well as with non-automated, stand-alone optical measuring apparatus.

Figure 2:
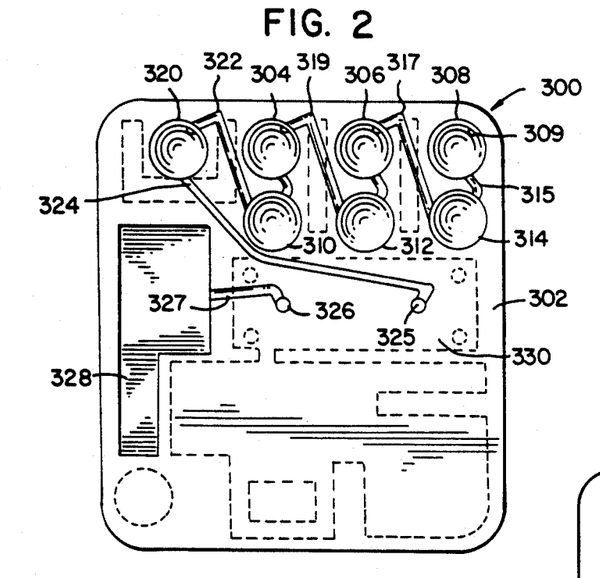
FIG. 2 is a plan view of the sample side of a centrifugal test cartridge of the type used with a conventional automated centrifugal assay instrument.
Figure 3:
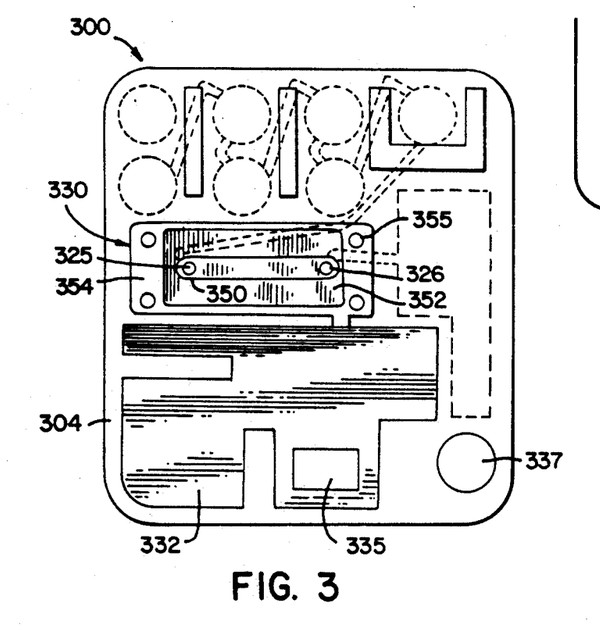
FIG. 3 is a plan view of the electronics side of the test cart illustrated in FIG. 2.

Referring to FIGS. 2 and 3, a multi-chamber test cartridge 300 of the type typically employed in the VISION ® instrument and which has been adapted for use with the first embodiment of the invention is illustrated. The test cartridge 300 has a sample side 302 and an electronics side 304 which are separated by a solid wall (not shown). On the sample side 302, sample chambers 304, 306 and 308 are provided for receiving and holding a first known calibration sample, unknown sample to be tested, and a second known calibration sample respectively. Each of the sample chambers 304, 306, and 308 has a small sample insertion opening 309 into which a volume of sample may be introduced by syringe or other conventional means. After a sample has been introduced therein, the openings 309 may be closed by adhesive tape or other similar means to prevent escape. Holding chambers 310, 312 and 314 corresponding to sample chambers 304, 306 and 308 respectively are also formed on the sample side of the test cartridge 300. Each sample chamber and corresponding holding chamber is connected by a narrow fluid passageway 315. In addition, holding chambers 312 and 314 are connected to adjacent sample chambers 304 and 306 respectively by narrow fluid passages 317 and 319 respectively. Holding chamber 310 is connected to a delivery chamber 320 by a narrow fluid passageway 322. The delivery chamber 320 is connected by a narrow fluid passageway 324 to an opening 325 which extends through the solid wall of the test cartridge 300 separating the sample 302 and electronics 304 sides into an electrode mounting well 330, which is described in detail below. The opening 325 is preferably located near a first longitudinal end of the electrode mounting well 330. A second opening 326 extends through the solid wall into the electrode mounting well 330 near the opposite longitudinal end thereof and is connected by a narrow fluid passageway 327 to a waste chamber 328 formed in the sample side of the test cartridge.

Referring to FIG. 3, the electronic side 304 of the test cartridge 300 has an electronics compartment 332 formed therein. The electronic components comprising the preferred transducer circuit means 210 of the first embodiment are mounted in the electronics compartment 332 and are preferably sealed by an epoxy or other fluid-tight sealant. In its most preferred form, the transducer circuit means 210 is embodied in a single hybrid integrated circuit chip. Alternatively, sufficient space is provided in the compartment 332 to accommodate a discrete embodiment of the transducer circuit means 210 as well. A window 335 comprising an opening in the surface of the electronic side 304 of the test cartridge 300 is formed immediately above the mounting location of the liquid crystal light valve which comprises the optical output means 220 of the preferred embodiment. In its most preferred form, the liquid crystal light valve 220 and the window 335 have a corresponding dimension of approximately ⅛ inch square. Alternatively, multiple windows and light valves could be provided in the cartridge 300 to allow multiple electrolyte measurements to be made simultaneously. In this case, the preferred transducer circuit means 210 would be duplicated for each light valve and the circuits would receive their inputs from the conductive areas of the electrode 200 in parallel. An alignment opening 337 is also preferably formed in the test cartridge 300 to facilitate mounting of the cartridge in the VISION ® instrument with the proper orientation.

Figure 4:
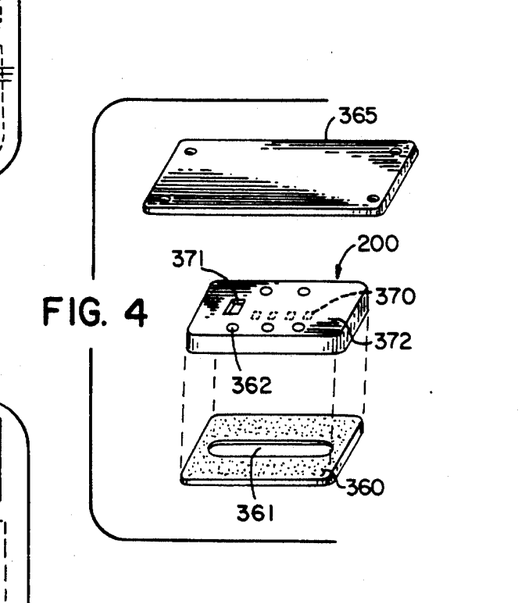
FIG. 4 is an exploded perspective view of an ion selective electrode, electrode mounting gasket, and electrode cover adapted to be mounted to the test cartridge illustrated in FIGS. 1 and 2.

Referring to FIGS. 3 and 4, the electrode mounting well 330 comprises an elliptical well portion 350 which extends longitudinally to encompass an area including both openings 325 and 326 from the sample side 302 of the test cartridge 300. The elliptical well portion 350 forms a sunken channel in a substantially rectangular counter-sunk electrode-receiving area 352 of the electrode mounting well 330. The electrode receiving area 352 is formed in a cover receiving area 354 which is slightly indented from the surface of the electronic side 304 of the test cartridge 300. The cover receiving area 354 has screw receiving openings formed therein in proximity to the four corners thereof. A gasket 360 preferably constructed of a silicon rubber or similar material suitable for forming a fluid-tight connection with the ion selective electrode 200 is formed in the shape of the electrode receiving area 352 and has an elliptical opening 361 formed therein corresponding to the elliptical channel 350. The gasket 360 is mounted flat in the electrode receiving area 352. The ion selective electrode 200, having a selected plurality of ion selective detection sites 370 and a reference electrode 371 on a first surface 372 thereof is mounted with the detection sites 370 and the reference electrode 371 facing downwardly atop the gasket 360 so that the detection sites 370 and the reference electrode 371 are aligned in the elliptical opening 361 of the gasket. The cover 365 is mounted in the cover receiving area 354 so that the top surface of the cover 365 is flush with the surface of the test cartridge 300. The cover 365 is preferably secured in place by screws (not shown) or other conventional fastening means. Alternatively, the cover 365 may be ultrasonically welded or otherwise permanently connected in place. The gasket 360 and the first surface 372 of the ion selective electrode 200 mate to form an elliptical fluid-tight channel about the detection sites 370 and reference electrode 371 in the channel 350. A plurality of flat conductive areas 362 on the ion selective electrode 200, are conductively connected with each of the detection sites 370 and the reference electrode 371. The conductive areas 362 are preferably connected to inputs of the transducer circuit means 210 by conventional light gauge electrical wire (not shown).

Figure 5:
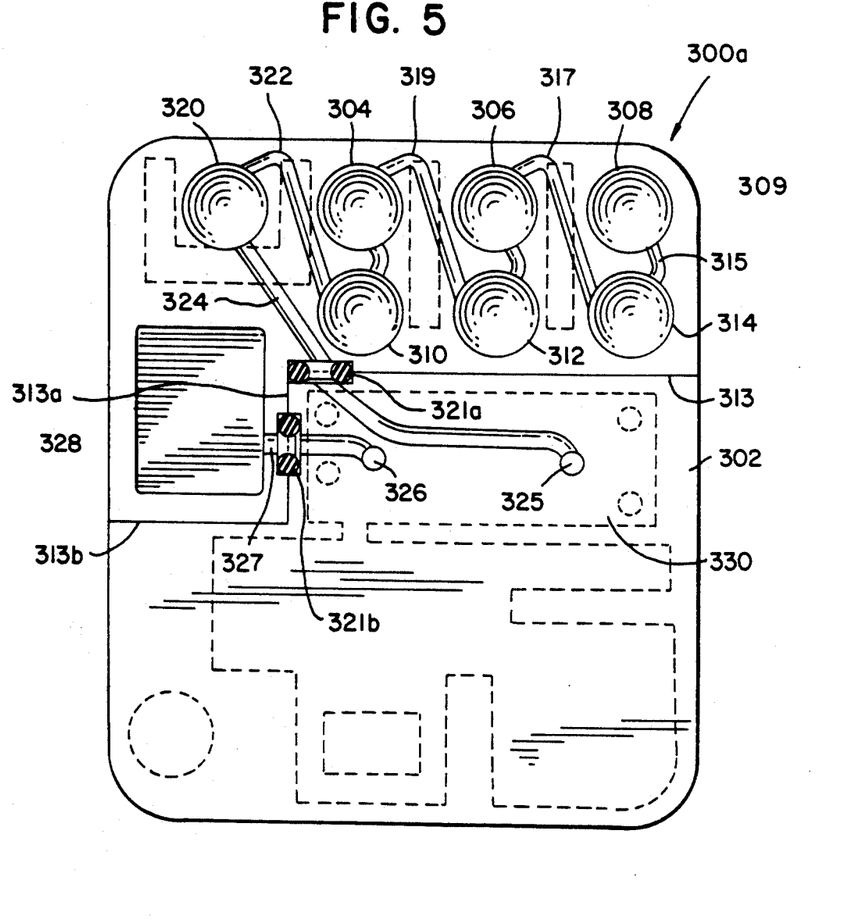
FIG. 5 is a plan view of the sample side of an alternative centrifugal test cartridge.

An alternative embodiment to the one piece test cartridge 300 is illustrated in FIG. 5. In the alternative embodiment the cartridge 300a has separate sample and electronics sections. In this embodiment, the first section of the cartridge 300a containing the sample and waste chambers is disposable and the second section containing the electronics is reusable. The two sections are advantageously divided along a horizontal line 313 extending from the edge of the cartridge 300a between the chambers 310, 312, 314 and the electrode mounting well 330, along a vertical line 313a between the electrode mounting well 330 and the waste chamber 328, and along a horizontal line 313b extending to the edge of the cartridge 300a below the waste chamber 328. The two sections are preferably connected by a slide mount or other suitable means. In the advantageous application of the first embodiment in centrifugal assay apparatus, which is described in detail below, the centrifugal force applied to the two sections may typically be in the range of 500 g's and assists in maintaining the two sections in fluid-tight connection. "0"-rings 321a, 321b and/or a sticky adhesive such as beeswax and rosin, paraffin, or a piezoelastic are provided to seal the separate sections at the fluid passageways 324 and 327. Additionally, connecting means such as locking tabs or the like (not shown) may also be provided if desired or if necessary for non-centrifugal applications.

With the VISION ® instrument, it is necessary to shield the test cartridge's sensitive electronics, such as the ISE 200 and transducer circuit means 210, from the noise generated by rotation of the test cartridge 300 on the VISION ® centrifuge. Suitable shielding can typically be accomplished by coating the test cartridge 300 with a metallic coating as is well known in the art.

An alternative embodiment to the two part test cartridge of FIG. 5 is illustrated in detail in previously referenced co-pending U.S. Ser. No. 07/337,011 now U.S. Pat. No. 4,940,327.

Operation of the first embodiment will now be described with reference to its particularly advantageous utilization in conjunction with the exemplary VISION ® centrifugal assay instrument described previously. In a preferred mode of operation, a first calibrator sample having a known, relatively low level concentration of one or more selected electrolytes of interest is introduced into the sample chamber 304 by suitable means such as a syringe. A second calibrator sample having a known relatively high concentration of the same electrolytes is introduced by suitable means into the sample chamber 308. The sample having unknown concentrations of the electrolytes of interest to be measured is introduced into the sample chamber 306. The test cartridge 300 is mounted in a test cartridge holder in the centrifuge of the assay instrument and is rotated at a high rate of speed, typically on the order of 1800 rpm's. The entire test pack 300 is then rotated by 90° which causes the calibrator samples and the unknown sample to be conducted from the respective sample wells 304, 306, and 308 to the corresponding holding chambers 310, 312, and 314 respectively. The test cartridge 300 is then rotated back to its original position, which causes the second calibrator sample to be conducted to the sample chamber 306, the unknown sample to be conducted to the sample chamber 304, and the first calibrator sample to be conducted to the delivery chamber 320. Next, the test cartridge 300 is again rotated by 90° which causes the unknown sample to be conducted to the holding chamber 310, the second calibrator sample to be conducted to the holding chamber 312, and the first calibrator sample to be conducted from the delivery chamber 320 into the fluid tight elliptical channel 350 where it comes into fluid contact with the detection sites 370 and reference electrode 371 of the ion selective electrode 200. Excess sample is conducted by the fluid passageway 327 into the waste chamber 328. In order to ensure an accurate and repeatable measurement of the selected electrolytes for which each of the detection sites 370 has an affinity, the test cartridge 300 is held in the rotated position for a minimum of approximately 15 seconds, during which time the first calibrator sample remains in contact with the detection sites 370 and reference electrode 371.

Each detection site 370 causes a voltage differential having a magnitude related to the concentration of the electrolyte for which the particular site has an affinity to be generated between the reference electrode and the conductive area corresponding to that site. As illustrated in FIG. 1, each voltage is coupled into the transducer circuit means 210 by the input buffer means 232, is level adjusted by the adjustment offset means 248, and is amplified by the linear amplifier 234. The magnitude of the electrical signal appearing at the output of the linear amplifier is linearly related to the concentration of the selected electrolyte. The oscillator means 242 and the inverting driver means 244 alternately actuate the first and second pairs of bilateral switches 236 to apply the electrical signal and ground to the contacts of the liquid crystal light valve 220 with alternating polarity. The liquid crystal light valve 220 responds to the alternating polarity drive signal by becoming opaque to a degree which is linearly-related to the magnitude of the electrical signal at the output of the linear amplifier means 234, i.e. the optical density of the light valve is linearly related to the magnitude of the electrical signal. The optical source 225 of the assay instrument is positioned to illuminate the liquid crystal light valve 220 on one side. The liquid crystal light valve 220 absorbs a portion of the light generated by the optical source 225 which is linearly related to the magnitude of the alternating polarity drive signal. The optical signal generated on the opposite side of the light valve 220 has intensity linearly related to the magnitude of the drive signal and to the optical density of the light valve 220. The optical density of the light valve 220, as indicated by the generated optical signal represents the concentration of the selected electrolyte in the sample. The optical signal is detected by the optical detector apparatus 230 of the assay instrument.

Subsequently, the test cartridge 300 is rotated between its original position and the 90° position in order to sequentially conduct first the unknown sample and then the second known calibrator sample into the fluidtight channel 350 and into fluid contact with the detection sites 370 and reference electrode 371 of the ion selective electrode 200 for measurement in the same manner as described above. The test cartridge 300 is preferably not rotated after the second calibrator sample is brought into fluid contact with the ion selective electrode 200 so that a level of fluid always covers the ion selective membranes to prevent air pocket formation or contamination.

Since the level of the input voltage differential is adjusted by the offset adjustment means 240, and the gain of the linear amplifier means 234 is adjusted by the resistors 246 and 247 so that the transducer circuit means 210 operates within the linear response range of the liquid crystal light valve 220, the concentrations of the electrolytes of interest in the unknown sample are easily determined by linear interpolation from the optical absorption or density values derived for the two known calibrator samples in the same manner as described in previously referenced U.S Ser. No. 196,120. Thus, in the first embodiment the optical absorption or densities represented by the optical signals corresponding to the first and second calibrator samples and the unknown sample are linearly interpolated to obtain the concentrations of the electrolytes in the sample rather than the integrated intensities or count values of the optical signals.

Figure 6:
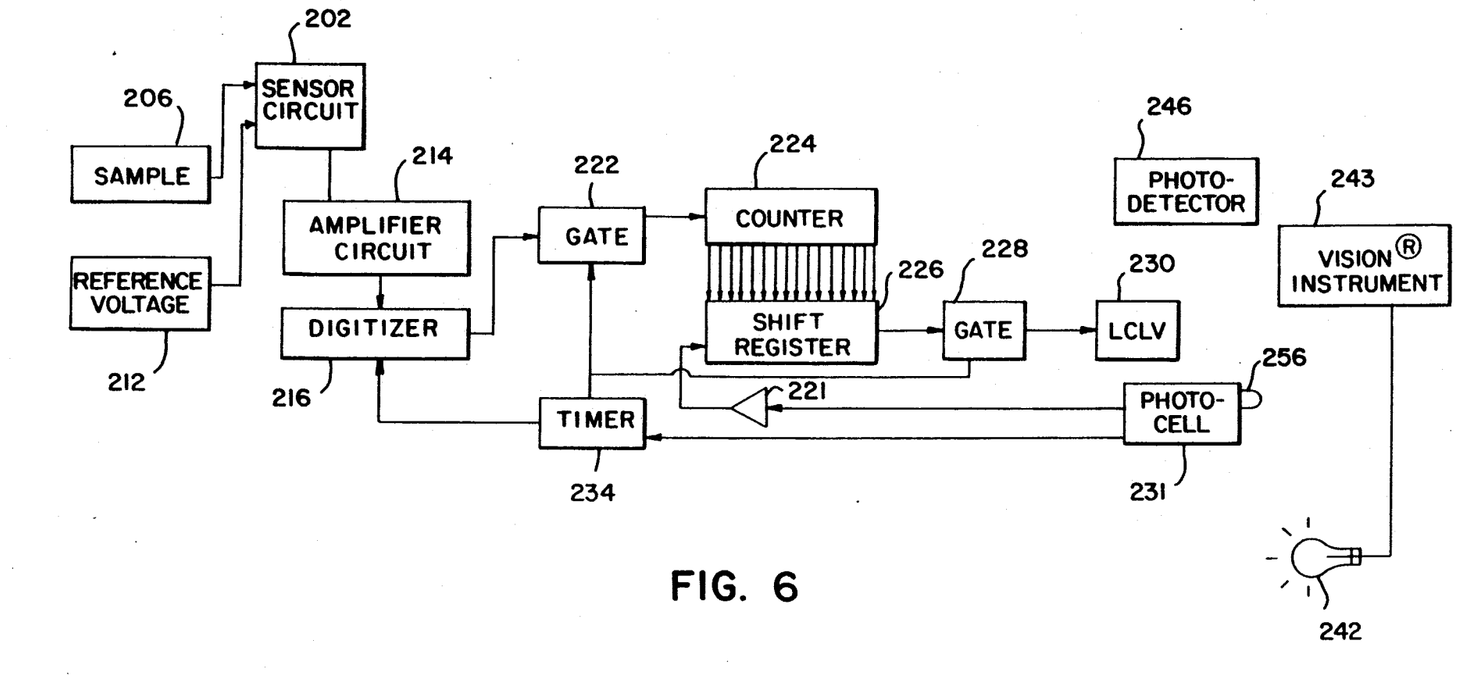
FIG. 6 is a block diagram of the digital electronics of the transducer circuit for a second equally preferred embodiment of the invention, illustrating the passive duplex transfer of data between a VISION ® instrument and the digital transducer.
Figure 7:
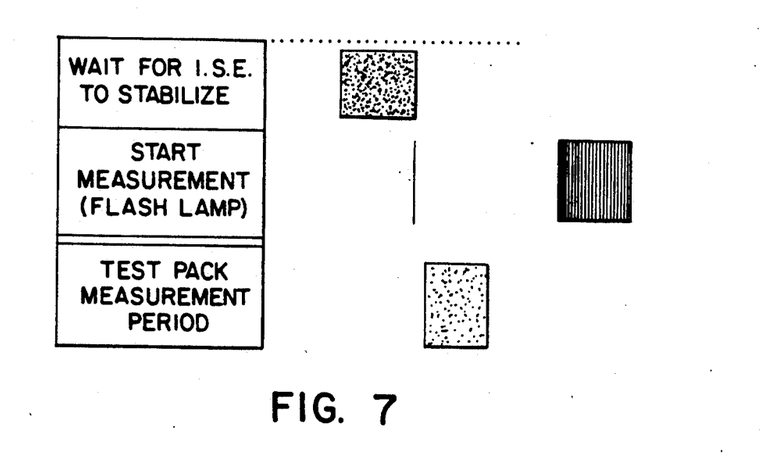
FIG. 7 illustrates the operational protocol for the digital electronics of FIG. 6.
Figure 8:
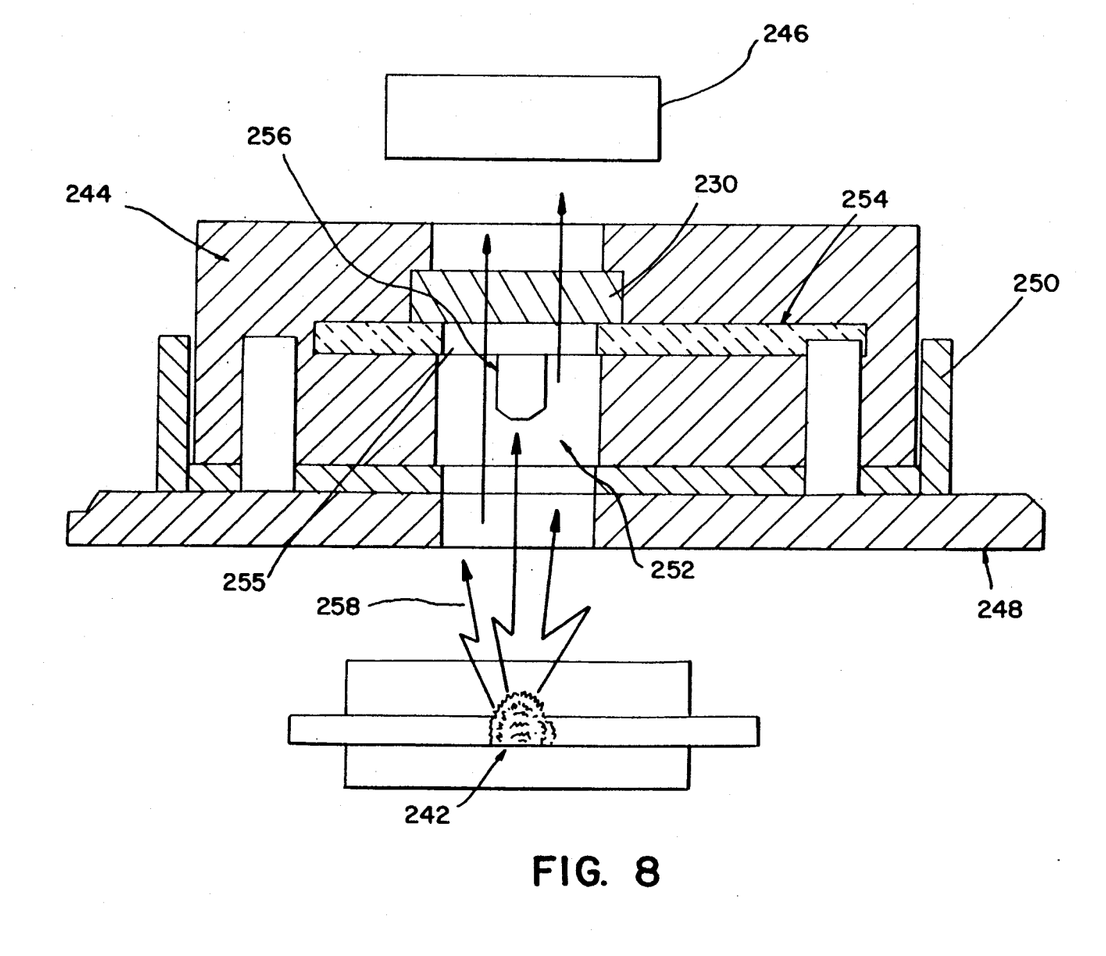
FIG. 8 is a diagram of the optical interface between the test cartridge and a VISION ® instrument, further illustrating the duplex transfer of data.

FIGS. 6-8 illustrate a second and equally preferred embodiment of the electrolyte measuring apparatus of the invention. This second embodiment generally comprises ion selective electrode means for generating a plurality of voltage differentials corresponding to the concentrations of a corresponding plurality of preselected electrolyte concentrations in a sample. The second embodiment also includes transducer circuit means for converting the voltage differentials to electrical signals having parameters related to the magnitudes of the voltage differentials, and optical means responsive to the electrical signals to generate optical signals having parameters related to the electrical signals and representative of the concentrations of the pre-selected electrolyte in the sample. As with the first embodiment, the second embodiment is employed in conjunction with the multi-chamber test cartridge and the VISION ® instrument described above. In contrast to the first embodiment, however, the second embodiment employs a variation of the transducer means and a duplex transmission configuration of the optical means which takes advantage of the photodetection properties of a light emitting diode (LED).

Referring generally to FIG. 6, there is shown a block diagram of the digital electronics of the transducer circuit for a second equally preferred embodiment of the present invention, illustrating the passive duplex transfer of data between the VISION ® instrument and the rotating test cartridge's digital transducer. A sensor circuit 202 typically comprises an ISE of the type previously described and shown in FIGS. 3 and 4. A sample 206 of interest is in contact with the sensing element (not shown) of the sensor circuit 202. A reference voltage circuit 212 generates a reference (or regulating) voltage and is applied as an input to the sensor circuit 202 as described herein. The sensor circuit's output, typically a potential difference, is amplified by an amplifier circuit 214 and is coupled to a voltage to frequency converter known as a digitizer 216.

The digitizer 216 is coupled to a first gate 222 which passes a gating pulse to a 16 bit binary counter 224 having serial input and parallel outputs. A timer 234, controlled by photocell 231, is coupled to first gate 222 and a second gate 228. Counter 224 operates a shift register 226 which, in turn, has an output coupled to second gate 228. Second gate 228 operates a liquid crystal light valve (LCLV) 230 via a buffer 221. It is noted here that particular circuit elements for carrying out the functions shown in FIG. 6 and described herein, are easily within the purview of one of ordinary skill in the art.

In operation the reference voltage circuit 212 provides a positive offset for the sensor circuit 202. Since the voltage generated by the sensor circuit 202 may go negative and the digitizer 216 will not, an offset voltage is required that is larger than any allowed negative sensor circuit 202 drift. The amplifier circuit 214 is used to obtain the high-input impedance that may be required by the sensor circuit 202, and also provides a voltage gain to match the input range of the digitizer 216.

The digitizer 216 generates a digital pulse train whose frequency is proportional to the instantaneous input voltage from amplifier circuit 214. If the pulses are counted over a fixed period of time, there is a binary number (count) that is proportional to the input voltage applied to the digitizer 216. Moreover, the count is a proportional average of the voltage applied over the time that counting occurs. This allows random noise occurring in the previous stages and the sensor circuit 202 to be averaged out.

The timer 234 dictates the precise interval that the first gate 222 is open so that the counter 224 can count the binary output from the digitizer 216.

The parallel inputs of the shift register 226 are connected to the parallel outputs from the counter 224. At the end of the counting sequence, the binary number in the counter 224 is transferred to the shift register 226 for storage and serial presentation to the LCLV 230. By transferring the count to the shift register 226 the counter 224 is free to acquire the next measurement. This allows the next measurement to occur while the previous measurement is being transferred to the VISION ® instrument's computer by way of the flash lamp 242 and the LCLV 230. This feature will be described in more detail below.

The photocell 231 is driven by a light emitting diode (LED) 256 and provides a signal to the timer 234 to begin the timing sequence. The photocell 231 also provides a signal, through a buffer 221, to the shift register 226 to initiate the shift of the next bit of the binary count out to the LCLV 230.

FIG. 8 illustrates a test cartridge 244 situated in a test cartridge holder 250 within the VISION ® instrument. The VISION ® flashlamp 242 projects a flash of light 258 up through the test cartridge 244 to the VISION ® photodetector 246. The flashlamp 242 is synchronized with the rotating VISION ® centrifuge disc 248 so that proper illumination is achieved. The VISION ® flashlamp 242 is strobed, generating an arc of high-intensity light 258. This high-intensity light 258 travels upward through the VISION ® centrifuge disc 248, the VISION ® test cartridge holder 250, and the window area 252 of the test cartridge 244. Within the window area 252 is the digital hybrid electronic board 254 having an opening 255 for mounting LCLV 230 and LED detector 256. The high-intensity light 258 passes through the test cartridge window area 252 and impinges upon the photodetector 246.

The digital hybrid electronic board 258 is made of rigid ceramic and is mechanically secured to the test cartridge 244. The LCLV 230 and the LED detector 256 are mounted to the ceramic board 258 and positioned inside opening 255. The LED 256 faces the flashlamp 242 and the LCLV 230 faces the photodetector 260. The LED 256 is mounted on the same axis as the LCLV 230, which means that the light passing through the test cartridge strikes the LED 256 and the LCLV 230 simultaneously. The LED 256 produces an electronic signal in response to the high-intensity light 258 which is sent to the digital hybrid electronics both to initiate measurement of the present potential and to shift the data from the immediately previous measurement. The LCLV 230 modulates the intensity of the incoming light 258 in a bistable fashion. The modulated light then reaches the Vision photodetector 246. The LED detector 256 is a standard LED which is used in an unconventional manner, i.e., as a photodetector. An LED is employed because it has a silicon diode junction similar to that of a photodetector except that its sensitivity is much less than that of a photodetector. In practical terms, this means that a photodetector is so sensitive that ambient room light may constantly activate it, whereas the relatively insensitive LED will generally be affected only by a high-intensity light.

FIG. 8 further illustrates the timing sequence for the digital electronics and the duplex data transfer between the VISION ® instrument and the test cartridge 244. The flash lamp 242 is strobed for the first time. At this stage the test cartridge 244 has been appropriately rotated to bring the first calibrator in contact with the sensor circuit 202 shown in FIG. 6, and a potential corresponding to the ion concentration of the calibrator is present at the sensor circuit 202 output. When the flash lamp 242 is strobed for the first time the potential present at the sensor circuit 202 output is converted to a digital pulse train by the digitizer 216 and the pulses are counted by the counter 224 over the measuring period. A single strobe from the flash lamp starts the counting and the counter ignores any further strobes from the flash lamp 242 until the measuring period is over. At the end of the first count the binary number stored in counter 224 is shifted in parallel out to the shift register 226. The flash lamp 242 is strobed again only this time the first strobe is followed by 15 more. The flash lamp 242 also controls the shift register 226 via the LED 256. Each strobe of the flash lamp 242 shifts a single bit of the binary number stored in the shift register 226 out to the LCLV 230. Since the flash lamp 242 is orders of magnitude faster in response time than the LCLV 230 an arbitrary unknown state exists in the LCLV 230 and that state is valueless during the first strobe of this sequence. Each subsequent strobe from the flash-lamp 242 shifts the next bit of the binary count to the LCLV 230 and simultaneously allows photodetector 246 to read the previous bit of the count value reflected in the LCLV 230. This simultaneous independent two-way transmission is referred to as passive duplex transfer. Fifteen (15) additional strobe pulses follow until the complete binary number is shifted out to the LCLV 230. The sequence is then repeated for the next measurement and transfer.

It is noted that the data is transferred very quickly (in microseconds) after the high intensity light pulse 258 is sent from the VISION® flashlamp 242, while the LCLV 230 requires longer periods of time to change. This means that the new bit presented by the shift register 226 is not read until the next flash. The VISION® flash lamp 242 strobes the shift register 226, via photocell 231 and buffer 221, and simultaneously allows the transparent or opaque state of the LCLV 230 to be read by the VISION® photodetector 246. Since the strobe lamp 242 is very fast and the LCLV 230 is very slow, the flash is completed long before the LCLV 230 can respond. This implies that the VISION® photodetector 246 reads the previous state of the LCLV 230 and not the current one. The VISION® instrument's mode of data acquisition therefore always lags by one bit. A similar strobing and measurement sequence occurs for the sample and second calibrator except for the first strobe.

The utilization of ISE technology and the digital passive duplex data transmission in conjunction with automated centrifugal assay instruments in the manner described above provides advantages particular to centrifugal-type electrolyte measuring apparatus. The rotating centrifuge environment puts greater demands on the electrolyte measuring device. The duplex digital transducer utilizes a simplified yet novel optical and digital configuration that reduces the possibility of errors and maintains accuracy even at centrifuge speeds of around 1800 rpms.

What have been described are certain aspects of apparatus for measuring electrolyte concentrations in fluid biological samples which constitute presently preferred embodiments of the invention. It is understood that the foregoing description and accompanying illustrations are merely exemplary and are not to be taken as limiting the scope of the invention, which is defined solely by the appended claims and their equivalents. Various changes and modifications to the preferred embodiments will be apparent to those skilled in the art. For example, the preferred ion selective electrode means utilized in the preferred embodiments may be replaced by chemical field effect transistor means which generate current as an electrical component indicative of electrolyte concentration rather than voltage. Such changes and modification can be made without departing from the spirit and scope of the invention. Accordingly, it is intended that all such changes and modifications be covered by the appended claims and their equivalents.

We claim:

1. Apparatus for use with centrifugal-type sample analyzers of the type having optical source means for providing a first optical signal and first optical detector means for detecting a modulated optical signal for measuring at least one parameter of at least one preselected electrolyte in a fluid sample, comprising:
   cartridge means adapted for use in a centrifugal apparatus;
   sample container means mounted in said cartridge means for containing a sample;
   sensor means mounted in said cartridge means in fluid-tight communication with said sample container means and operative when in fluid contact with said sample to generate at least one electrical signal having magnitude related to at least one parameter of at least one said preselected electrolyte in said sample;
   transducer means mounted in said cartridge means electronically connected to said sensor means and responsive to said at least one electrical signal generated by said sensor means, said transducer means capable of generating at least one second signal in response to said first signal having a parameter related to the magnitude of said at least one electrical signal;
   second optical detector means mounted in said cartridge means for intercepting the path of said first optical signal, said second optical detector means being capable of generating at least one third signal in response to said first optical signal, said third signal being electronically connected to said transducer means to control the output of said second signal from said transducer; and
   optical means mounted in said cartridge means for intercepting the path of said first optical signal and being responsive to said at least one second signal for absorbing a portion of said first optical signal to generate said modulated optical signal.

2. The apparatus defined in claim 1 wherein said at least one electrical signal is an analog signal and said at least one second signal is a digital signal.

3. The apparatus defined in claim 2 wherein said transducer means includes:
   pulse generator means responsive to said analog signal for generating a plurality of pulses; and
   counter means for counting said pulses to generate said digital signal comprising a count value related to the concentration of said preselected electrolyte in said sample.

4. The apparatus defined in claim 3 wherein said transducer means further includes means for converting said digital signal to a bit-serial digitally encoded pulse train for communication to said optical means, said optical means being responsive to said pulse train to generate said modulated optical signal.

5. The apparatus defined in claim 1 wherein said optical means comprises liquid crystal light valve means having crystal polarization responsive to said second signal for absorbing a portion of said first optical signal to generate said modulated optical signal.

6. The apparatus defined in claim 1 wherein said first optical signal is a high-intensity light.

7. The apparatus defined in claim 6 wherein said second optical detector means is a light emitting diode.

8. The apparatus defined in claim 1 wherein:

said transducer means includes measurement means capable of generating said at least one second signal in response to said first signal and storage means connected to said measurement means capable of accepting said second signal and holding a previously measured second signal, said second signal having a parameter related to the magnitude of said at least one electrical signal;

said third signal being electronically connected to said measurement means to control the output of said second signal from said measurement means to said storage means;

said third signal also being electronically connected to said storage means to initiate the transfer of said previously measured second signal to said optical means;

said optical means intercepting the path of said first optical signal and being responsive to said previously measured second signal for absorbing a portion of said first optical signal to generate said modulated optical signal.

9. The apparatus defined in claim 8 wherein said at least one electrical signal is an analog signal and said at least one second signal is a digital signal.

10. The apparatus defined in claim 9 wherein said measurement means includes pulse generator means responsive to said analog signal for generating a plurality of pulses.

11. The apparatus defined in claim 10 wherein said storage means includes:

counter means for counting said pulses to generate said digital signal comprising a count value related to the concentration of said preselected electrolyte in said sample; and means for converting said digital signal to a bit-serial digitally encoded pulse train for communication to said optical means, said optical means being response to said pulse train to generate said modulated optical signal.

12. Apparatus for use in an analyzer having optical source means for providing an optical signal and first optical detector means for detecting an optical signal, said apparatus comprising:

a cartridge defining a sample containing means adapted to contain a sample;

sensor means mounted in said cartridge to sense a parameter of said sample and operative to generate at least one first electrical signal having a characteristic related to the parameter of said sample;

second optical detector mounted in said cartridge and adapted to produce a first control signal in response to receipt of said optical signal;

transducer means mounted in said cartridge and being operative to generate a second electrical signal in response to said control signal and said first electrical signal, said second electrical signal having a characteristic related to the characteristic of said first electrical signal; and optical absorbing means mounted in said cartridge for receiving said optical signal and operative to modulate the amount of said optical signal to reach the first optical detector in response to said second electrical signal.

13. The apparatus defined in claim 12 wherein said cartridge is in motion relative to said analyzer having said optical source and said first optical detector.

14. The apparatus defined in claim 12 wherein said second optical detector is a light emitting diode.

15. The apparatus defined in claim 12 wherein said second electrical signal generated by said transducer means is a digital signal.

16. Apparatus for use with a centrifugal-type sample analyzer of the type having optical source means for providing a first optical signal and first optical detector means for detecting a modulated optical signal for measuring at least one parameter of at least one preselected electrolyte in a fluid sample, comprising:

sensor means in fluid contact with the sample to generate at least one electrical signal having a magnitude related to at least one parameter of at least one preselected electrolyte in the sample;

transducer means responsive to said first signal and capable of generating at least one second signal in response to said first signal, said second signal having a parameter related to the magnitude of said at least one electrical signal;

light emitting diode means for intercepting the path of said first optical signal and producing at least one third signal in response to said first optical signal;

said third signal being electronically connected to said transducer means to control the output of said second signal from said transducer; and optical means responsive to said at least one second signal and intercepting the path of said first optical signal for absorbing a portion of said first optical signal to generate the modulated optical signal.

17. The apparatus defined in claim 16 wherein said first optical signal is a high intensity light.

* * * * *

UNITED STATES PATENT AND TRADEMARK OFFICE
CERTIFICATE OF CORRECTION

PATENT NO. : 5,134,359

DATED : July 28, 1992

INVENTOR(S) : Benton A. Durley, III and Carl M. Groom

It is certified that error appears in the above-identified patent and that said Letters Patent is hereby corrected as shown below:

Line 2 of the Abstract, after "samples" insert --is provided--.

Column 16, line 3, after "detector" insert --means--.

Column 16, line 15, after "response to" insert --[the characteristic of]--.

Signed and Sealed this

Twenty-fourth Day of August, 1993

Attest:

BRUCE LEHMAN

Attesting Officer

Commissioner of Patents and Trademarks